(12) United States Patent
Gallas et al.

(10) Patent No.: US 8,133,414 B2
(45) Date of Patent: Mar. 13, 2012

(54) LIGHT FILTERS USING YELLOW MELANIN AND MELANIN-LIKE OLIGOMERS AND PHOTOCHROMIC DYES

(75) Inventors: James M. Gallas, San Antonio, TX (US); Ira Hessel, San Antonio, TX (US)

(73) Assignee: Photoprotective Technologies, Inc., San Antonio, TX (US)

( * ) Notice: Subject to any disclaimer, the term of this patent is extended or adjusted under 35 U.S.C. 154(b) by 0 days.

(21) Appl. No.: 12/313,115

(22) Filed: Nov. 17, 2008

(65) Prior Publication Data

US 2010/0123105 A1   May 20, 2010

(51) Int. Cl.
 *G02B 5/23* (2006.01)
 *B01D 15/08* (2006.01)
 *C02F 1/28* (2006.01)
(52) U.S. Cl. ........ 252/586; 210/656; 351/159; 359/350; 359/355; 359/356; 359/361; 359/642; 428/412; 428/441; 523/106; 524/110
(58) Field of Classification Search ...... 606/9; 351/159; 428/1.1, 1.3, 412, 441; 359/642, 350, 355, 359/356, 361; 524/110; 252/586; 210/656; 523/106
See application file for complete search history.

(56) References Cited

U.S. PATENT DOCUMENTS

2005/0053729 A1 * 3/2005 Bourdelais et al. ............ 428/1.1

FOREIGN PATENT DOCUMENTS

WO   WO 93/23480     * 11/1993
WO   WO 2007/130656 A2 * 11/2007

OTHER PUBLICATIONS

Edward Fahey, Julian B. Chaudhuri, Molecular characterisation of size exclusion chromatography refolded urokinase-plasminogen activator, Chemical Engineering Science 56 (2001) 4971-4978. Elsevier Science Ltd. All rights reserved.*

* cited by examiner

*Primary Examiner* — Ling Choi
*Assistant Examiner* — Bijan Ahvazi

(57) ABSTRACT

Selective fractionation and separation of melanin and use of fractionated or separated melanin in connection with light filters is disclosed. Further, light filters that use yellow melanin or melanin like materials prepared to have a yellow color and a melanin transmission spectrum in combination with a photochromic dye are disclosed. The yellow form of melanin has minimal impact on the perception of light intensity with transmission values greater than 80%. The combination allows for a single light filter suitable for both night driving and sunglass applications and which also preserve color perception.

7 Claims, 7 Drawing Sheets

LIGHT FILTERS USING YELLOW MELANIN AND MELANIN-LIKE OLIGOMERS AND PHOTOCHROMIC DYES

TECHNICAL FIELD OF THE INVENTION

This invention relates to the field of melanins and, more particularly, to the preparation and use of yellow melanin as a pigment to provide ultra-violet, visible and near infrared absorption. Further, the invention relates to the use of melanin in combination with photochromic dyes as a radiation absorbing pigment in ophthalmic devices, protective eye wear and other similar media suitable for providing protection from radiation. Further, the invention relates to the fractionation of melanin for use as absorbing pigment in ophthalmic devices, protective eye wear and other similar media suitable for providing protection from radiation.

BACKGROUND OF THE ART

The reduction of high energy visible (HEV) light is useful in light filters because this reduction leads to reduced glare and increased eye protection. Also, the eye is much less sensitive to HEV (the violet and blue) light; so its reduction does not impact on the perception of adequate light intensity for normal vision. Melanin is a very useful pigment for the reduction of high energy visible light because it is able to reduce violet and blue without disturbing color perception. However, melanin occurs naturally in different colors (red, yellow, brown) and not all filter the HEV light in the same way.

U.S. Pat. No. 5,112,883 to James M. Gallas describes the broad use of melanin lenses in such light filters. More recently, in U.S. patent application Ser. No. 10/850,228 of Sugimura, Hideyo (published on Jan. 13, 2005), entitled "Photochromic Plate Containing Melanin," melanin has been proposed to be used in combination with photochromic dyes because such a combination would provide a lightly-tinted HEV-absorbing lens (melanin alone) that would darken in light because of the presence of the photochromic dye (hereinafter referred to as the '228 application. However, the melanin described by the '228 application uses a brown melanin. While this brown melanin does reduce HEV light more than the non-HEV light at 550 nm—where the eye is most sensitive—the difference in the transmission is insignificant. That is, the brown melanin in the Sugimura patent will tend to also reduce a significant amount of green light as well as HEV light—unless the melanin concentration is low. However, if the melanin concentration is too low, then the use of melanin to reduce glare and offer protection from sunlight damage will have very little efficacy. This difficulty arises because the filtration is being shared by both melanin and a second dye (the photochromic dye). For this reason, Sugimura was forced to limit the concentration of melanin, and therefore its range of transmission. It ranged from 40% to 80%. This transmission range would preclude a very important application of the concept of a high energy visible (HEV) lens in combination with a photochromic dye in night driving lenses, which by European standards, cannot be lower than 80%.

The use of yellow melanin in accordance of the present invention as a filtering pigment offers several advantages over the prior art. These advantages will become evident in the following description.

BRIEF SUMMARY OF THE INVENTION

In order to make an effective HEV reducing melanin-photochromic dye system, it is necessary to use a special melanin that is yellow. Such a system would allow significant HEV reduction and yet very high luminous transmission values of greater than 80% because the transmission spectrum of the yellow melanin has very low values where the eye is least sensitive and high values where the eye's sensitivity is greatest. In this system, filtration is due only to the yellow melanin and at low light intensities—such as for computer use or in the case of night driving. Then under stronger light conditions, a photochromic dye would be activated and provide the darkening needed for outdoor sunlight use.

These points are best illustrated by the curves of FIG. 1. In FIG. 1, curve "series 2," illustrates the sensitivity of the human eye to visible light. It peaks at about 550 nm (green light). It also shows that the eye is very insensitive to light in the wavelength region between 400 and 450 nm (blue light). Of course, the graph also shows that the eye is equally insensitive to red light between 650 and 700 nm. Both series 1 and series 3 curves of FIG. 1 show the transmission of melanins. The curve of series 3 is a brown melanin that is presently produced by Photoprotective Technologies, Inc. of San Antonio, Tex. Series 1 curve shows the transmission of a yellow melanin disclosed herein and made in accordance with the present invention. The yellow melanin makes feasible the goal of reducing HEV light adequately—by having a low transmission in the violet and blue and still having a high transmission in the wavelength region where the eye is most sensitive. The brown melanin is not suitable because its transmission is too low in the region where the eye is most sensitive.

BRIEF DESCRIPTION OF THE FIGURES IN THE DRAWINGS

For a detailed description of the present invention, reference will now be made to the accompanying drawings wherein:

FIG. 1 depicts three graphs wherein series 1 curve illustrates the transmission spectrum of yellow melanin, series 2 curve illustrates the sensitivity of the human eye to visible light and series 3 curve illustrates the transmission spectrum of brown melanin;

DETAILED DESCRIPTION OF THE INVENTION

Figure 4:
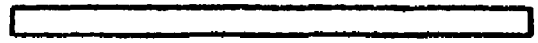
FIG. 4 is a diagram of a transparent solid substrate light filter, containing a yellow dyeing agent such as yellow melanin, a yellow form of the polymerization product of 3hydroxy-kynurenine, a yellow form of an asphaltene or a yellow form of a maltene and also a photochromic dye uniformly distributed throughout the thickness of the light filter.
Figure 5:
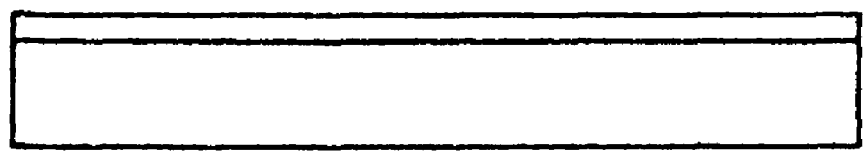
FIG. 5 is a diagram of a transparent solid light filter in which one or both of the dyes is contained in a thin region which is nominally 5 to 15 microns at the surface of the light filter 2.
Figure 6:
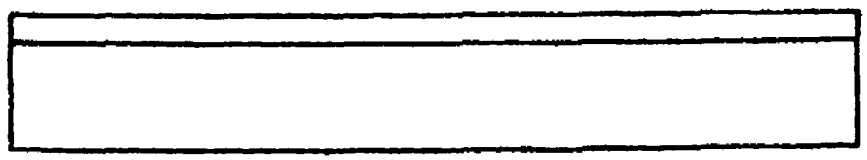
FIG. 6 is a diagram of a transparent light filter in which one or both of the dyes is contained in a thin hard coating which is nominally 5 to 15 microns at the surface of the light filter 2.
Figure 7:
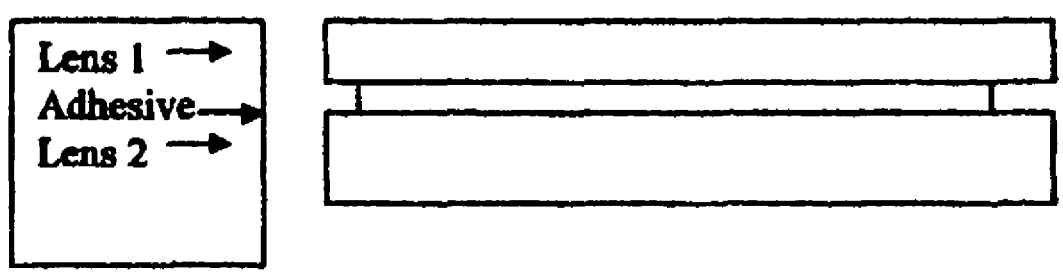
FIG. 7 is a diagram of a laminated lens system in which either the yellow melanin or the photochromic dye, or both, is dispersed in an adhesive between two lenses and the remaining dye is dispersed in one of the two lenses.

The term "solid transparent substrate", as used in this patent application, is a solid object made of a clear glass or a polymer, and generally taking the form of a light filter. Examples of such are, but not limited to, flat or curved sheets of plastic or glass such as sunglass lenses, ophthalmic lenses, intraocular lenses, windows, contact lenses, and computer screens. A diagram of a transparent solid substrate that may or may not contain a dye is shown in FIG. 4.

The term "thermoset" process, as used herein, is a process in which the plastic by the action of an oxidizer or initiator acting upon a monomeric liquid, causing the monomer to polymerize. The term "thermoplastic" process refers to the process in which the plastic is already formed and is caused to flow or become liquified by the action of heat and pressure.

The term "uniformly dispersed" means that the synthetic lens pigment shall be mixed sufficiently well within the solid transparent substrate that there is negligible light scatter or haze when objects are viewed through the solid transparent substrate that contains the dye.

Figure 1:
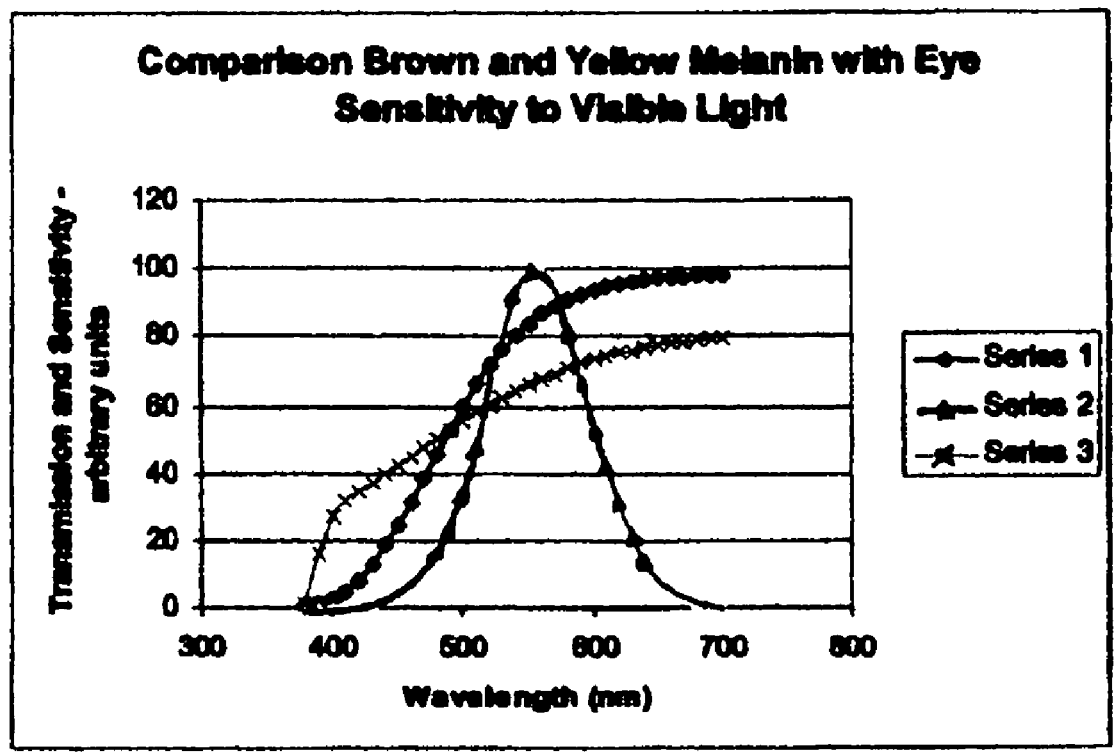

One of the essential features of this invention is to make a lens apparatus that uses a melanin, or a melanin like dye, that is processed in such a way that its transmission spectrum follows, as closely as possible, the shape of the eye sensitivity curve series 2 of FIG. 1. Such a melanin or melanin-like dye will, in general, have a yellow color and can be processed in several ways to achieve such a transmission spectrum. The term "melanin like dye" refers to a dye that has a transmission spectrum similar to that of melanin. In accordance with the present invention, such dyes are a yellow form of the polymerization product of 3hydroxy-kynurenine, a yellow form of an asphaltene or a yellow form of a maltene In general, melanin consists of a distribution of molecular weights and particle sizes. There is also heterogeneity in its chemical structure reflected in properties such as molecular polarity. Because of this, standard techniques can be used to separate and isolate different portions of a melanin sample according to both size and polarity. Generally the smaller sized units will have less absorption in the red end of the optical spectrum and will therefore appear more yellow.

In addition to the techniques mentioned above, melanins can be prepared that already tend to be yellow. This can be obtained by disrupting the conjugation of the synthesizing melanins by including certain other molecules besides the standard melanin precursors. Another method for making a yellow melanin is to bleach or oxidize the melanin sample after it is already polymerized. Such oxidation could affect both the conjugation and the particle sizes. Finally, any combination of the above mentioned techniques can be used to produce a yellow melanin.

Hydrophilic yellow melanin can be formed by first synthesizing melanin in the standard way, in aqueous media, by using a standard melanin precursor, like dopamine, an oxidizer, like potassium persulphate, and by raising the pH—and then followed by bleaching with hydrogen peroxide. Further fractionation to select smaller molecular weight portions of the melanin can be achieved by adding increasing amounts of a solvent miscible with water but which, because of it different polarity, selectively precipitates the larger molecular weight portions of the melanin. Thus different segment of the molecular weight or size distributions can be obtained by adding varying amounts of a co-solvent such as tetrahydrofuran.

Hydrophilic yellow melanin can also be formed as described above, but with the addition of L-cysteine during the synthesis and this is described in the melanin scientific literature. L-cysteine is added in comparable molarity along with a standard melanin precursor such as L-Dopa and a suitable oxidizer such as potassium persulphate and by raising the pH.

In the preferred embodiment, hydrophobic melanin is prepared according to the methods described in U.S. Pat. No. 5,112,883 and in a European patent by Gallas (WO9323480), by transferring aqueous melanin to an organic solvent such as acetonitrile or tetrahydrofuran and then derivatizing it with a suitable derivatizing agent such as methcryloyl chloride. Smaller molecular weight fragments can be obtained by adding a second organic solvent of lower polarity in varying amounts causing increasing amounts of derivatized melanin to precipitate. Thus, continuously different molecular mass sections of melanin can be isolated. In particular, the smallest molecular weights will remain in the double solvent system—and hence be isolated—when the highest concentrations of the second solvent are present.

Applicant has found further that a yellow melanin can be made—by bleaching or oxidizing the smaller molecular weight fractions of the derivatized melanin described above—with the transmission spectrum shown in FIG. 1, series 1 above.

Another particular feature that makes melanin so attractive for optical filters is its ability to reduce HEV light without disturbing the perception of color. Applicant has been able to use the Farnsworth Munsell 100 color test to confirm this advantage of melanin filtration. More significantly, melanin's ability to preserve color perception applies and extends to the case of yellow melanins—even though yellow dyes used in filters generally disturb the perception of color for those wearing such light filters.

This optical performance characteristic of melanin must relate to its optical absorption or optical transmission spectrum and although these spectra vary among red, brown and yellow melanins, one aspect remains constant. That aspect is that all of the absorption spectra are monotonically-increasing functions of energy—throughout the entire visible spectrum of wavelengths and well into the UV region. Furthermore the primary differences occur on the red end of the optical spectrum (melanins with greater optical density in the region 600 nm to 700 nm appear more brown).

One of the essential features of this invention is to attain a lens apparatus that uses a yellow melanin, or a yellow melanin-like dye that has a transmission spectrum that follows, as closely as possible, the shape of the eye sensitivity curve of FIG. 1 and which also preserves the perception of color with luminous transmission in the dark greater than 80%, and in combination with a photochromic dye which, when activated in sunlight will have a total luminous transmission of between 10% and 20%.

Photochromic Dyes

Figure 2:
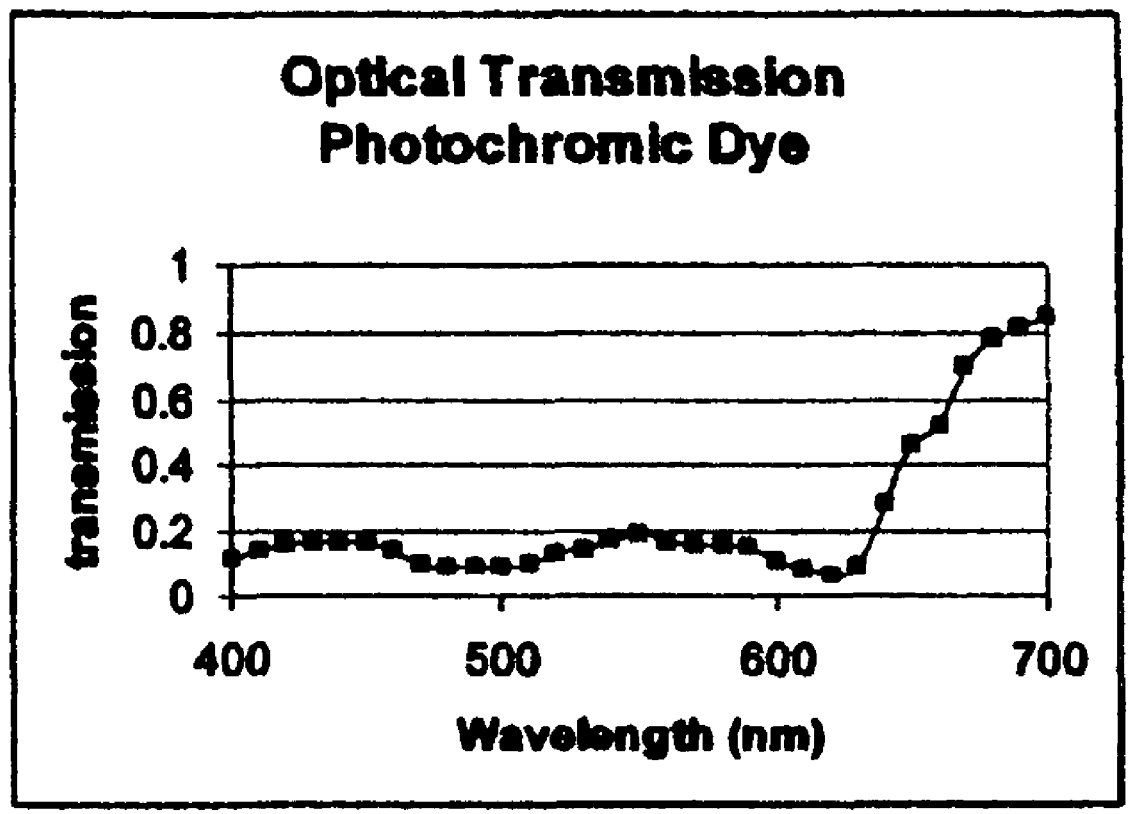
FIG. 2 is a graph that shows the transmission spectrum of a combination of two photochromic dyes, namely, indolino spironaphthoxyazines and pyridobenzoaxine.

There are many commercially available photochromic dyes that absorb light in the visible range of wavelengths and the particular choice of a photochromic dyes to be used in this invention is not a significant issue. A transmission spectrum of one such dye is shown in FIG. 2. The transmission spectrum is a combination of two photochromic dyes—indolino spironaphthoxyazines and pyridobenzoaxine. However, in the context of this invention, any photochromic dye—or combination of photochromic dyes—that transmit light throughout the visible region of wavelengths, and which are used at concentrations so as to yield a luminous transmission values of 10% to 20% when activated in sunlight are acceptable.

Preparation of Selectively Precipitated or Fractionated Melanin

Melanins are highly-irregular, nanometer-sized, sheet-like polyphenols which tend to aggregate under a variety of chemical and physical conditions including intermolecular stacking forces, solution pH, and the presence of metal ions in solution. Scientific research suggests that in any synthetic melanin product, there is a range of molecular weights. Different sections of this molecular weight distribution may also have different polarities. Both molecular weight and polarity can impact on the dispersability of a polymer in a solvent system or in a melt flow system as in a thermoplastic, injection molding process. In order to achieve good dispersion and low haze levels in lenses made with melanin, chemical derivatization is carried out on aqueous melanin as described in U.S. Pat. No. 5,112,883. In such chemical modifications, melanin is transferred from water to an organic solvent such as methylene chloride or tetrahydrofuran (THF) where it is treated with a derivatizing agent—such as methcryloyl chloride or methylchlorofromate. To obtain a powder form suitable for compounding with the thermoplastic lens material, the organic solvent containing the derivatized melanin is then injected into a solvent with an appropriate polarity such as petroleum ether or hexane in which the derivatized melanin is insoluble.

In a non-selective precipitation, the ratio of hexane volume to the THF volume is about 10 to 1 with the result that more than 90% of the melanin is precipitated. The precipitated melanin is then filtered and dried in a vacuum oven. The powder can then be used in a thermoplastic process just as any other dye powder.

While dispersion in liquid plastic resin—in a thermoset or in a thermoplastic process—is greatly improved by derivatization, haze levels in some thermoplastics like acrylic and polycarbonate are still in the range of 2% to 4%. Applicant has found that significant improvement in haze is achieved when derivatized melanins are further purified or isolated by selective precipitation.

In such selective precipitation, hexane is added to the methylene chloride-melanin solution gradually, and in relatively small volume increments—in stages. For example, in the first stage, hexane is added to the methylene chloride-melanin solution, in a volume ratio of 1 (hexane) to 3 (methylene chloride-melanin solution). In this initial stage, only a small portion or fraction of the melanin precipitates. This material is filtered out with filter paper and dried, while the majority of the melanin remains in solution. The filtered and dried portion is hereinafter referred to as Portion I. Then, in a second stage, an additional volume of hexane is added to the same melanin-methylene chloride solution so that a higher ratio of hexane to the melanin-methylene chloride solution is achieved—for example a ratio of 1:2. In this case, some more melanin precipitates out of the solution and is also filtered, dried and collected. The filtered and dried portion is hereinafter referred to as Portion II. In a third stage, additional hexane is added to achieve a ratio of 1:1 and an additional amount of melanin is precipitated and filtered and dried. This filtered and dried portion is hereinafter referred to as Portion III. Finally, an additional amount of hexane is added to the material remaining in solution to achieve a ratio of 3:1. The precipitated material is collected in filter paper and dried and this filtered and dried portion is hereinafter referred to as Portion IV.

Applicant has found that melanin powder Portions II, III and IV will dissolve in diethylene glycol bis-allylcarbonate (trade name CR39) very well and at concentrations appropriate for sunglass darkness (about 15% luminous transmission) at a path length of 1.5 mm. However, CR39 is the liquid monomer resin of a thermoset polymer. Applicant has further found that Portion II will cause haze in a thermoplastic application; applicant has further found that Portion IV will not cause haze in either acrylic or polycarbonate and that Portion III will cause haze in polycarbonate but no haze in acrylic.

In summary, applicant has found that melanin that remains in solution at higher ratios of petroleum ether or hexane or, in general, solvents with very low polarity will have less haze than melanin that precipitates with low ratios or amounts of low polarity solvent.

Preparation of Yellow Melanin

Applicant has further found that it is possible to produce a yellow melanin powder by oxidation of the derivatized melanin from Portion IV.

PREFERRED EMBODIMENTS

In the first preferred embodiment, yellow melanin is dissolved into a liquid thermoset monomer such as CR39 and an ophthalmic lens is made from a casting of this material in an appropriate mold. A photochromic dye is then adsorbed or imbibed or tinted onto the surface of the lens—generally using heat and relying on diffusion of the photochromic dye into the surface of the plastic lens.

In a second preferred embodiment, yellow melanin is compounded with a thermoplastic such as polycarbonate and an ophthalmic lens is made in an injection molding process using an appropriate mold. A tintable hard coat is applied to the surface of the lens and a photochromic dye is then adsorbed or imbibed or tinted onto the surface hard coating on the surface of the lens—generally using heat and relying on diffusion of the photochromic dye into the surface of the hard coating.

While melanin can be compounded and injection molded into a thermoplastic optical lens of approximately 1.5 mm, or incorporated into a thermoset plastic lens as described in the preferred embodiments, other lenses that are more wafer-like and having a thickness of less than 1 mm are possible options as well. The photochromic dye is then imbibed into the surface of the yellow melanin-containing thermoplastic lens.

The combination of a melanin dye and a photochromic dye in an ophthalmic lens system can occur in a variety of other ways—all of which are obvious configurations to those skilled in the art. These include co-dissolving yellow melanin and photochromic dyes with an optical thermoplastic in a suitable solvent system and then allow the solvent to evaporate resulting in a film that contains the dyes. Alternatively, both dyes can be imbibed into the surface of a lens in a tinting process. Alternatively, both dyes can be co-dissolved in a thermoset optical plastic resin that is poured into a mold and allowed to cure to form an optical lens. If it is necessary to avoid any melanin-photochromic dye interactions, then the two dyes can be introduced separately into these plastics. For example, the yellow melanin powder can be co-dissolved with an optical thermoplastic in a suitable solvent system and then allow the solvent to evaporate resulting in a film that contains only the yellow melanin; then the formed film can be adhered or bonded to a solid plastic lens that contains the photochromic dye formed previously in one of the standard ways such as a compounding process.

Figure 3:
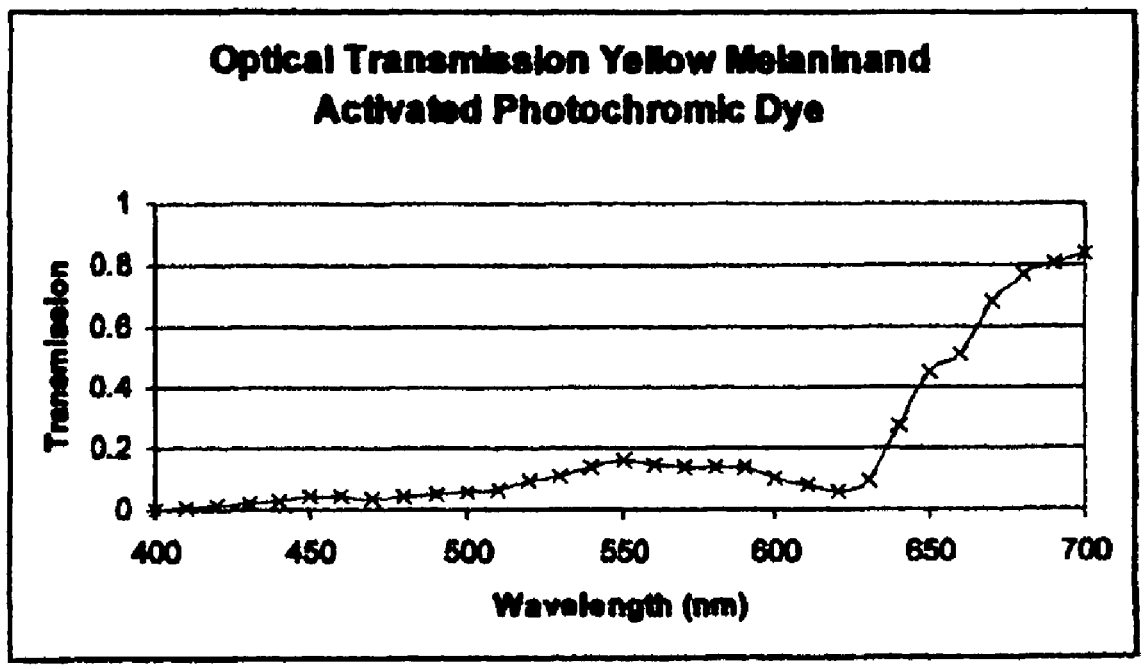
FIG. 3 is a graph that shows the total transmission of the yellow melanin and the photochromic dye of FIG. 2 in the sunlight-activated state.

When such combination of lenses is carried out the final sunlight-activated transmission will have the transmission of the melanin—multiplied at each wavelength—by the transmission of the photochromic dye as, for example, the transmission of the yellow melanin of FIG. 1 and the photochromic dye of FIG. 2 shown in FIG. 3.

Purification and Reduction of Haze by Size Exclusion

Melanin can also be fractionated to different fractions by passing solutions of melanin, preferably derivatized melanin, though a size exclusion chromatography column to separate the melanin according to size. Applicant has also found that further haze reduction can be achieved by further purification of melanin for use as an absorption medium using size exclusion chromatography techniques. The lowest molecular weight fractions present in the derivatized melanin solution that pass through a size exclusion column were found to contribute to the haze in lenses and that elimination of these lowest molecular weight fractions reduced the haze levels from about 2 to 4% to less than 1%. These lowest molecular weight fractions could occur systematically in the production process as either impurities or components of the raw materials. They could include, for example, one of the monomer precursors to melanin such as tyrosine, dopamine or catechol; they could also include the derivatized forms of these precursors; they could also include various peroxidation inhibitors present in the solvents, such as BHT that is known to be present in THF.

Fractionation in Silica Gel Column

Melanin can also be fractionated to form fractions of melanin that are suitable for use in lenses or similar media with low haze by placing a solution of melanin, preferably derivatized melanin, on silica gel column and interacting it with solvents of increasing polarity passing through so that melanin fractions are separated according to polarity.

Similar procedures as described herein for the preparation, processing and use of yellow melanin having low haze may be used in accordance with the present invention to prepare, process and use a yellow form of the polymerization product of 3hydroxy-kynurenine, a yellow form of an asphaltene or a yellow form of a maltene. Like the yellow melanin, the yellow form of the polymerization product of 3hydroxy-kynurenine, the yellow form of an asphaltene or the yellow form of a maltene may be used as a yellow filter agent to form a light filter having a low haze.

The following examples further illustrate the invention but are not to be construed as limitations on the scope of the invention contemplated herein.

Example 1

Preparation of Selectively Fractionated

Portion IV Melanin

Ten (10) grams of derivatized melanin obtained from Photoprotective Technologies, Inc. of San Antonio, Tex., was dispersed in 100 mL of tetrahydrofuran (THF) by stirring for 1 hour. 100 mL of hexane was added next drop-wise over a period of 1 hour. The precipitated material was separated and an additional 200 mL of hexane was added drop-wise to the material that remained suspended to obtain a hexane to THF ratio of 3:1. The precipitated material (Portion IV) was collected and dried.

Example 2

Preparation of Yellow Melanin from Fractionated Melanin 1. 340 mg of selectively precipitated Portion IV melanin and 1.50 g of benzoyl peroxide were dissolved in 20 mL of THF in a 50 mL round bottom flask 2. The reaction vessel was fitted with an air cooled condenser.
3. The reaction was placed in a water bath which was heated from 60-640 C for 20 h.
4. The reaction was removed from the heat, cooled and poured into 80 mL of hexane over 20 sec with swirling.
5. The precipitate was allowed to settle and the supernatant poured off.
6. 20 mL of THF was added and the material quickly dissolved. This was poured into 70 mL of hexane over 20-30 sec with swirling. Fluffy precipitate appeared quickly and after 20 min the supernatant was filtered.
7. The material was allowed to dry and yielded about 240 mg of yellow melanin.
8. The spectra of the yellow melanin is shown in series 1 curve of FIG. 1.

Example 3

Preparation of a Yellow Melanin Photochromic Lens System

One hundred (100) mg (0.1 g) of yellow melanin, as prepared in Example 2. was dissolved in 100 g of CR39 (diethylene glycol bis-allylcarbonate), trade name of PPG. The system was heated to 55 degrees Celsius and three grams of benzoyl peroxide was dissolved and the mixture was poured into a glass lens mold with a spacing of 1.5 mm. The temperature of the mold was increased gradually over three hours and the solid plastic lens was removed. It had a transmission of 85% at 550 nm.

A mixture of two photochromic dyes, indolino spironaphthoxyazines and pyridobenzoaxine was uniformly dispersed in a Loctite adhesive and several drops were placed onto the lens of Example 1 containing the yellow melanin. A second clear lens with the same radius of curvature as the first lens was pressed against the first lens to form a laminated lens. The concentration of the photochromic dyes was adjusted to give the optical spectrum shown in FIG. 3 for the laminated lens under light-activated conditions.

Example 4

Yellow Melanin and Photochromic Dye

Yellow melanin powder was dissolved into liquid CR39 monomer resin at a concentration so as to yield an optical transmission of about 85% at 550 nm for a lens of thickness 1.5 mm. The transmission spectrum of this lens is represented by the curve of series 1 in FIG. 1. Subsequently, a combination of two photochromic dyes—indolino spironaphthoxyazines and pyridobenzoaxine was used to imbibe the yellow melanin-CR39 lens to give a sunlight-activated optical transmission of about 20% at 550 nm. The resulting transmission is shown in FIG. 3.

Example 5

Various lots of melanin were derivatized and selectively fractionated to produce a Portion IV type and dried to a powder as described in Example 1. Polycarbonate (PC) lenses were injection molded using this powder at a melanin-to-PC mass ratio of 1:800. The luminous transmission of lenses thus formed were typically in the range of 40% to 45% with a lens thickness value of 1.4 mm. An average haze value, over 5 lenses was 2.2 with value ranging from about 2% to 4%.

Example 6

Size Exclusion Chromatography

Figure 8:
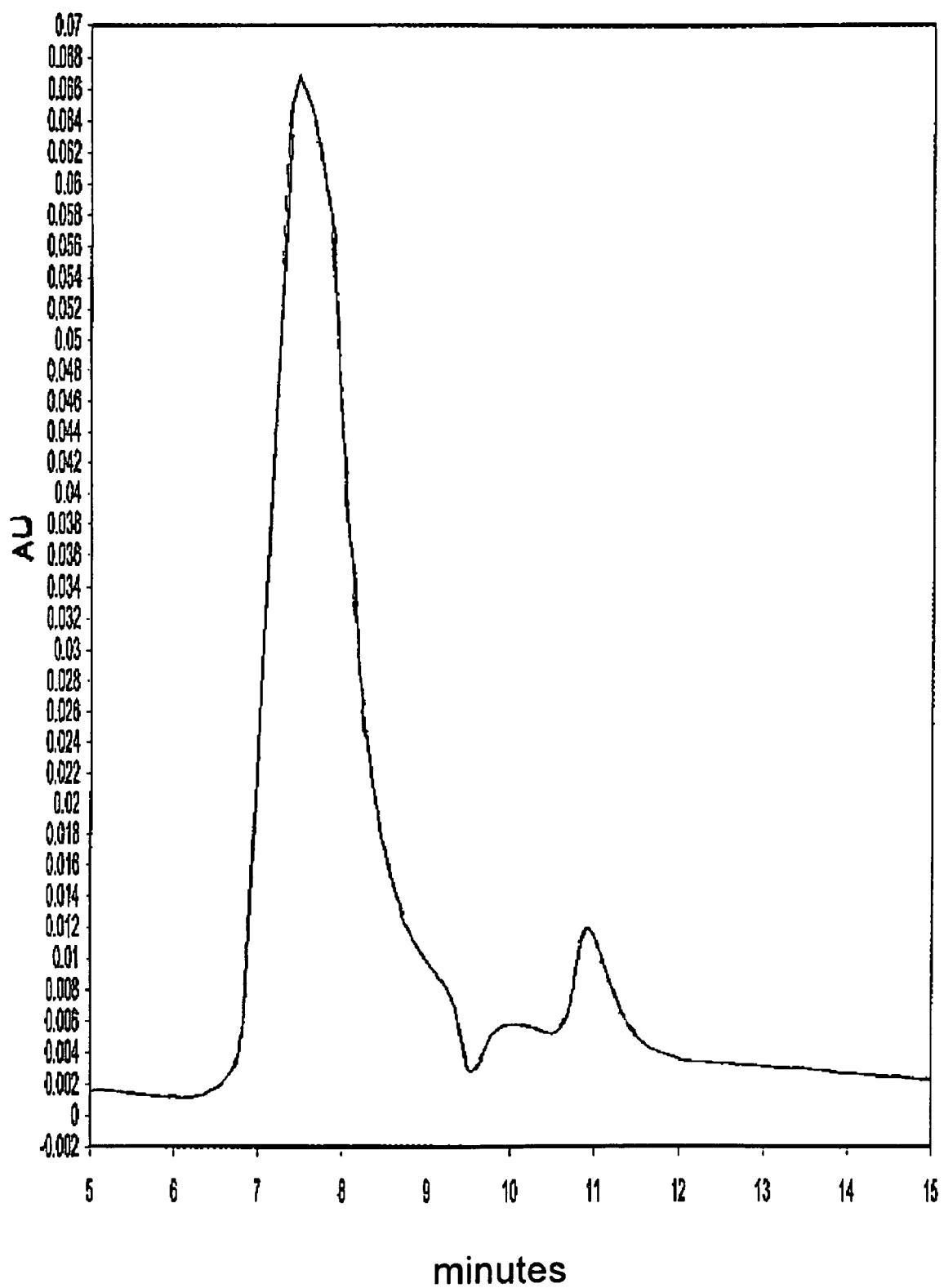
FIG. 8 is a graph showing the optical absorbance (or AU) for various molecular weight fractions of melanin obtained in accordance with the present invention.

A dilute solution of portion IV melanin, 1 mg/mL, from Example 1 was made with THF and injected into a Jordi 1000 angstrom chromatography column with dimensions of 10×250 mm. Recent melanin research literature suggests that melanins are oligomeric structures with a distribution of molecular weights that may range from 1000 to 4000. It is possible that smaller molecular weight fractions—less than 800, and consisting of dimmers and trimers—are present following the synthesis, and also impurities introduced by the solvents used in the derivatization process. In the size exclusion column, the smaller molecular weight particles will take more time to pass through the column because they will spend time diffusing within the pores of the gels comprising the column—provided the column is chosen properly. The larger particle fractions of the melanin will not enter the pores and, instead, will pass between the gel particles and pass through the column more quickly. A typical distribution spectrum is shown in FIG. 8. The graph suggests that the major component elutes through the column at approximately 7.5 to 8 minutes, but that there are also smaller molecular weight fractions that take longer—9, 10 and 11 minutes to pass through.

Figure 9:
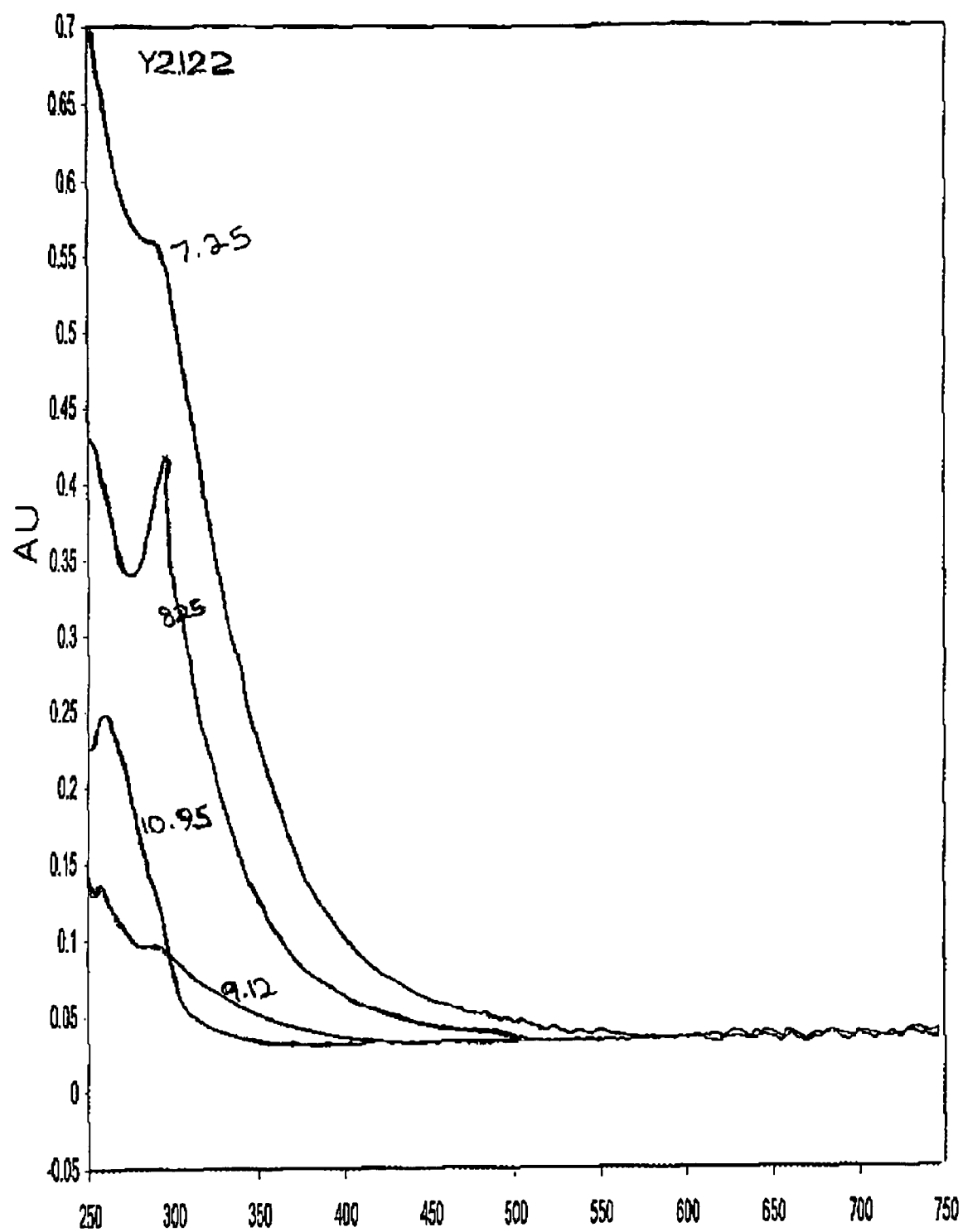
FIG. 9 is a graph showing the optical absorption spectra for the various molecular fractions of melanin obtained in accordance with the present invention.

A second set of spectra—optical spectra were recorded that corresponded to selected times: 7.25 minutes, 8.25 minutes, 9.12 minutes and 10.95 minutes. These spectra are shown in FIG. 9. The optical spectrum corresponding to 7.25 minutes refers to the largest fraction of the eluted material and has the expected absorption spectrum characteristic of melanin. The optical absorption spectrum corresponding to 8.25 minutes has a form more associated with bleached melanin or a melanin with a smaller degree of conjugation. These would be the small molecular weight fractions of melanin—but still considered to be melanin.

The optical spectra corresponding to elution times of 9.12 minutes and 10.95 minutes have no optical density in the wavelength region associated with visible light and therefore are not considered melanin.

A significant feature of this application is that applicant has found that melanin lots that have low concentrations of low molecular weight, non-melanin fractions have less haze. In FIG. 8, for example, small molecular weight fractions have absorption units (AU's) of magnitude up to 0.01.—for Portion IV melanin. Under these conditions unacceptable haze values of approximately 2% occur for lenses made with such melanin powders. However, when steps are taken to minimize the presence of the these fractions, by reducing the AU units to a magnitude of less than 0.002, the haze is reduced to levels of less than 1% which are acceptable by the ophthalmic industry.

Applicant has found that steps to reduce the presence of the low molecular weight fractions described above include the following: repeated resuspension of derivatized melanin powder in high grade or HPLC grade THF solvents and subsequent precipitations into HPLC grade hexane, for example. In these cases it is sufficient to test each lot of production derivatized melanin in an appropriate size exclusion column to confirm that one has achieved adequately low levels of low molecular weight fractions in the melanin powder. Other methods to reduce the presence of low molecular weight fractions include molecular sieves and also other solvent systems for suspension of melanin and precipitation of the melanin suspension.

While the invention has been described herein with reference to certain specific materials, procedures and examples, it is understood that the invention is not restricted to the particular materials, combinations of materials and procedures selected for the purpose of illustrations. Numerous variations of such details can be employed by those skilled in the art within the scope of this invention which is defined by the appended claims.

What is claimed is:

1. A method of preparing a light filter for providing protection from radiation, comprising the steps of:
   subjecting a mixture containing melanin to chromatography;
   separating at least one melanin fraction from the mixture by size exclusion to obtain a first melanin fraction;
   separating a second melanin fraction from the mixture to obtain a second melanin fraction; and combining melanin from the first melanin fraction with a transparent substrate to form the light filter having a haze level of less than 1%.

2. The method according to claim 1, wherein the transparent substrate is a glass material.

3. The method according to claim 1, wherein the transparent substrate is a plastic material.

4. The method according to claim 3, wherein the plastic material is diethylene glycol bis-allyl carbonate material.

5. The method according to claim 3, wherein the plastic material is polycarbonate material.

6. The method according to claim 3, wherein the plastic material is nylon material.

7. The method according to claim 3, wherein the plastic material is polyurethane material.

* * * * *